United States Patent
Panigrahi

(10) Patent No.: US 6,682,744 B1
(45) Date of Patent: Jan. 27, 2004

(54) PRO-GUT MATURATION AND ANTI-INFLAMMATORY EFFECTS OF LACTOBACILLUS AND LACTOBACILLUS SECRETED PROTEINS, CARBOHYDRATES AND LIPIDS

(75) Inventor: Pinaki Panigrahi, Columbia, MD (US)

(73) Assignee: University of Maryland, Baltimore, MD (US)

( * ) Notice: Subject to any disclaimer, the term of this patent is extended or adjusted under 35 U.S.C. 154(b) by 354 days.

(21) Appl. No.: 09/635,176

(22) Filed: Aug. 9, 2000

Related U.S. Application Data

(60) Provisional application No. 60/147,792, filed on Aug. 9, 1999.

(51) Int. Cl.$^7$ .................. A61K 39/02; A61K 39/00; A61K 38/00; A01N 63/00; C07K 1/00

(52) U.S. Cl. .................. 424/234.1; 424/93.45; 424/262.1; 424/184.1; 514/2; 530/350; 530/825

(58) Field of Search .................. 514/2; 530/350, 530/825; 424/234.1, 184.1, 242.1, 93.45

(56) References Cited

U.S. PATENT DOCUMENTS

| | | |
|---|---|---|
| 4,689,266 A | 8/1987 | Eckler |
| 5,411,751 A | 5/1995 | Crissinger et al. |
| 5,413,785 A | 5/1995 | Nanji |
| 5,439,678 A | 8/1995 | Dobrogosz et al. |
| 5,645,830 A | 7/1997 | Reid et al. |
| 6,132,710 A | 10/2000 | Panigrahi et al. |

FOREIGN PATENT DOCUMENTS

| | | | |
|---|---|---|---|
| WO | WO 90/09398 | * | 8/1990 |
| WO | WO 97/14802 | * | 4/1997 |

OTHER PUBLICATIONS

Bernet et al. Gut 35: 483–489, 1994.*
Kliegman et al. J. Pediatr. 95: 287–289, 1979.*
Edmund BJ. Am. J. Dis. Child. 133: 971, 1979.*
Zetterstrom et al., "Early Infant Feeding and Micro–Ecology of the Gut," Acta Paediatrica Japonica, 36, pp. 562–571, (1994).
Link–Amster et al., "Modulation of a Specific Humoral Immune Response and Changes in Intestinal Flora Mediated through Fermented Milk Intake," FEMS Immunology and Medical Biology, 10, pp. 55–64, (1994).
Bomba et al., "Colonization of the Digestive Tract of Gnotobiotic and Conventional Lambs with the Defined Lactoflora," Vet. Med., 39(11); pp. 701–710, (1994).
Bomba et al., "Interactions of Lactobacillus SPP. And Enteropathogenic *Escherichia Coli* Under In Vitro and In Vivo Conditions," Vet. Med., 41(5), pp. 155–158, (1996).

Sullivan et al., "Inhibition of Growth of Clostridium Botulinum by Intestinal Microflora Isolated from Healthy Infants," Microbial Ecology in Health and Disease, vol. 1, pp. 179–192, (1988).
Millar et al., "Enteral Feeding of Premature Infants with Lactobacillus GG," Archives of Disease in Childhood, 69, pp. 483–487, (1993).
Bernet et al., "Lactobacillus Acidophilus LA 1 Binds to Cultured Human Intestinal Cell Lines and Inhibits Cell Attachments and Cell Invasion by Enterovirulent Bacteria," 35, pp. 483–489, (1994).
Greene et al., "Factors Involved in Adherence of Lactobacilli to Human Caco–2 Cells," Applied and Environmental Microbiology, vol. 60, No. 12, pp. 4487–4494, (1994).
Conway, "Lactobacilli: Fact and Fiction," The Regulatory and Protective Role of the Normal Flora, pp. 263–281, (1988).
Caplan et al., "Bifidobacterial Supplementation Reduces the Incidence of Necrotizing Enterocolitis in a Neonatal Rat Model," Gastroenterology, 117, pp. 577–583, (1999).
Kapoor et al., "Differential Induction of Cytokine mRNA by Gram Negative and Gram Postive Bacterial Infections in a Rabbit Ileal Loop Model of Necrotizing Enterocolitis," The American Pediatric Society and the Society for Pediatric Research 1999 Abstract Form, (1999).
Srinivas et al., "Role of Bacteria and Immunosuppressive Agent in a Weanling Rabbit Ileal Loop Model of Necrotizing Enterocolitis," The American Pediatric Society and the Society for Pediatric Research 1999 Abstract Form, (1999).
Panigrahi et al., "Occurrence of Necrotizing Enterocolitis May Be Dependent on Patterns of Bacterial Adherence and Intestinal Colonization: Studies in Caco–2 Tissue Culture and Weanling Rabbit Models," Pediatric Reseach, vol. 36, No. 1, pp. 115–121, (1994).
Gupta et al., "Endemic Necrotizing Enterocolitis: Lack of Association with a Specific Infectious Agent," Pediatr. Infect. Dis. J., vol. 13, No. 8, pp. 728–734, (1994).
Panigrahi et al., "*Escherichia coli* Transcytosis in a Caco–2 Cell Model: Implications in Neonatal Necrotizing Enterocolitis," Pediatric Research, vol. 40, No. 3, pp. 415–421, (1996).
Gewolb et al., "Stool Microflora in Extremely Low Birthweight Infants," Arch. Dis. Child Fetal Neonatal Ed., 80, pp. F167–F173, (1999).

(List continued on next page.)

*Primary Examiner*—S. Devi
(74) *Attorney, Agent, or Firm*—Piper Rudnick LLP; Steven B. Kelber

(57) ABSTRACT

Strains of Lactobacilli having the ability to reduce or block pro-inflammatory cytokines and also to induce anti-inflammatory cytokines are disclosed. These strains may be used to prepare therapeutic agents that reduce inflammation. Lactobacillus secreted proteins, carbohydrates and lipids are also disclosed. The Lactobacillus secretions, which block translocation of bacterial agents such as Gram (–) bacteria, other infectious agents, toxins, chemicals and injurious substances, may be used in the prevention and treatment of inflammation caused by bacterial translocation and injury and in treating gastrointestinal dysfunctions.

7 Claims, 5 Drawing Sheets

OTHER PUBLICATIONS

Panigrahi et al., "Role of Glutamine in Bacterial Transcytosis and Epithelial Cell Injury," Journal of Parenteral and Enteral Nutrition, vol. 21, No. 2, pp. 75–80, (1997).

Conway et al "Products for inhibiting adhesion, growth and/or survival of pathogens comprises Lactobacillus metabolites including high mo. wt. protein compounds" Abstract, Derwent Database WO 9009398, 1990.

Honsha "Cytokine generation accelerator used in blood—comprises polysaccharide–glycan complex" Abstract, Derwent Database JP 08092122, 1996.

Claassen et al. "New and safe oral' live vaccines based on Lactobacillus" Abstract, Database Caplus, CAS (Columbus OH, USA) Access No. 1995:970093, Adv. Exp. Med. Biol. 1995 371B, p. 1553–1558.

* cited by examiner

PRO-GUT MATURATION AND ANTI-INFLAMMATORY EFFECTS OF LACTOBACILLUS AND LACTOBACILLUS SECRETED PROTEINS, CARBOHYDRATES AND LIPIDS

This application claims priority to U.S. Provisional Patent Application Ser. No. 60/147,792, filed Aug. 9, 1999, the entire contents of which are incorporated herein by reference.

BACKGROUND OF THE INVENTION

1. Field of the Invention

The present invention relates to Lactobacillus secreted proteins, carbohydrates and lipids and other anaerobic bacterial strains known to exert effects similar to Lactobacillus strains and their use in the prevention and treatment of inflammation. The Lactobacillus secreted proteins, carbohydrates and lipids of the invention can be used to protect intestinal cells against injury caused by disease, infectious agents, toxins, chemicals and other injurious substances. The Lactobacillus secreted proteins, carbohydrates and lipids of the invention can be used, in particular, to prevent and treat neonatal necrotizing enterocolitis.

2. Background of the Prior Art

Digestive problems, which comprise the number one health problem in North America, appear to be occurring with more frequency in recent years. One way to maintain digestive health is to maintain proper intestinal flora. Like many groups of living things, bacteria have "friendly" and "unfriendly" populations. Friendly bacteria play a major role in balancing and counteracting the unfriendly bacteria. When friendly bacteria are not at appropriate levels and when unfriendly bacteria dominate the intestinal flora, health problems can result, including intestinal toxicity and malabsorption of nutrients.

Lactobacilli are one of the most important types of friendly bacteria found in the digestive tract. The bacteria, which are named because they are able to turn milk sugar into lactic acid, play a key role in producing fermented milk, yogurt and cheese. In the early 1900's, Elie Metchinkoff hypothesized that Lactobacilli would provide a hostile environment to unfriendly bacteria in the intestinal environment. This hypothesis was later proven correct.

Lactobacilli have long been known to have positive effects in the intestine especially in maintaining a healthy gut microflora. These organisms generally act when they are available at the action site (intestine) live to exert their effects. These organisms are also known to secrete antimicrobial substances known as bacteriocins, i.e., substances that kill closely-related strains of other bacteria.

Bacterial translocation, i.e., the passage of viable intestinal bacteria across the intestinal epithelial cell layer into the normally sterile extra intestinal tissues, of few bacteria is a normal process and the mucosal immune system (macrophages as first line of defense) along with the consequent immune activation generally prevent detrimental translocation. Secretory immunoglobulins may also prevent the attachment of the same bacteria to the mucosal surface. Bacterial translocation has been suggested to play a role in the etiology of posttraumatic infections and multiple organ failure. This is presumed to be due to breakdown of the intestinal mucosal barrier, permitting pathogenic bacteria to pass into the blood stream.

Lactobacilli are known to prevent pathogenic microorganisms from colonizing on body surfaces (colonization resistance). Administration of antibiotics has a profound effect of the normal flora and can result in colonization with antibiotic-resistant organisms. Antibiotic-mediated disruption on the normal flora can thus lead to infection and its sequele. Commercial preparations of Lactobacilli have been used to restore normal intestinal flora after imbalance created by antibiotic therapy.

Despite significant advances in recent neonatal practice, neonatal necrotizing enterocolitis (NEC) remains a major cause of morbidity and mortality in premature infants. Survivors of NEC can also have considerable long-term morbidity resulting from the disease, including short-gut syndrome, failure to thrive, intestinal stricture and the need for repeated surgery. Although 11% of premature infants born weighing less than 1500 g develop NEC, the cause of the disease remains unclear and no specific treatments are available. A reasonable hypothesis suggests that a combination of factors including prematurity, intestinal ischemia and bacterial colonization lead to stimulation of an inflammatory cascade and a resulting final common pathway of NEC.

Bacterial colonization of the neonatal gastrointestinal tract begins when the infant encounters maternal cervical and vaginal bacteria during delivery. Brooke et al., Aerobic and anaerobic bacterial flora of the maternal cervix and newborn gastric fluid and conjunctiva: A prospective study, Pediatrics, 63:451–455 (1979). By 10 days of age, the majority of healthy full-term newborns are fully colonized with a variety of bacterial species. Long et al., Development of anaerobic fecal flora in healthy newborn infants, J. Pediatr., 91:298–301 (1977). The gut of a premature infant, in contrast, does not provide for proper colonization of the normally heterogeneous bacterial flora and rather demonstrates delayed colonization with only a limited number of bacterial species. Gupta et al., Endemic necrotizing enterocolitis: lack of association with a specific infectious agent, Pediatr. Infect. Dis., 13:725–734 (1994). It has been shown that the stool of preterm infants, with and without NEC, is colonized on the average by fewer than 2.5 species of aerobic bacteria, compared to >10 species in full terms. Gupta et al. (1994). It is believed that limited friendly bacterial colonization at least in part permits pathogenic bacterial overgrowth that could in turn initiate the cascade of events that lead to NEC.

Human milk populates the intestine with Bifidobacteria and Lactobacilli, generating a very different gut flora than that seen after formula feeding. Kevworth et al., Development of cutaneous microflora in premature neonates, Arch. Dis. Child, 67:792 (1992). A number of investigators have found decreased numbers of Lactobacilli in preterm infants; the reduction being correlated with antibiotic therapy and time spent in the incubator. Hall et al., Factors influencing the presence of fecal lactobacilli in early infancy, Arch. Dis. Child, 65:185–188 (1990).

A variety of in vitro studies indicate that endogenous intestinal bacteria can inhibit pathogenic bacteria. For example, Sullivan et al., Inhibitions of growth of C. botulinum by intestinal microflora isolated from healthy infants, Microbial. Ecology in Health and Disease, 1:179–192 (1988), showed that gut isolates of Bfidobacteria, Lactobacilli, Proprionibacteria and Enterococci inhibit *C. botulinum* in vitro. Numerous in vivo studies also lend support to the ability of selected Lactobacilli to modify the intestinal microflora. Conway, Lactobacilli: Fact and fiction, Ch. 16 in The regulatory and protective role of the normal flora, Grun, Midvedt and Norin, eds., Stockton Press, pp. 263–281 (1988).

Studies indicate that it is possible to successfully modify the gut flora in preterm infants by orally administering Bifidobacteria and Lactobacilli during and after antibiotic therapy.

Copending U.S. patent application Ser. No. 08/818,995, the entire contents of which are incorporated herein by reference, discloses that two strains of Lactobacillus, i.e., *Lactobacillus acidophilus* and *Lactobacillus plantarum*, reduced tissue injury and inflammatory cell infiltration, suggesting that they are useful in prevention and/or treatment of NEC.

Rubaletti et al., Probiotics Feeding Prevents Necrotizing Enterocolitis in Preterm Infants: A Prospective Double-Blind Study, Pediatric Academic Societies and American Academy of Pediatrics Joint Meeting (May 2000), discloses that Lactobacillus GG supplementation reduces the occurrence of NEC and urinary tract infection in pretern infants.

U.S. Pat. No. 5,413,785 discloses a method for reducing the quantity of endotoxin in blood plasma that includes administering Lactobacillus and a biocompatible carrier into the gastrointestinal tract.

Thus, the clinical use of Lactobacillus to enhance intestinal defense against potential luminal pathogens has been tested in vivo; however, an understanding of the mechanisms responsible for the observed protection is lacking. There thus exists a need to understand the underlying mechanisms responsible for Lactobacilli's beneficial effects in preventing and treating infection and inflammation.

SUMMARY OF THE INVENTION

Elevated levels of proinflammatory cytokines have been demonstrated in blood and tissue samples from babies with NEC. It has previously been shown that adherent *E. coli* can cause NEC-like injury in a rabbit ileal loop model and that Gram (+) acteria can block such injury.

The present inventor has surprisingly discovered that certain strains of Lactobacilli have the ability to reduce or block pro-inflammatory cytokines and that these strains also induce anti-inflammatory cytokines. Such effects have important ramifications in the host; permitting the use of Lactobacilli to prepare vaccines against inflammatory disease, as well as to prepare therapeutic agents to reduce inflammation if the disease has already been established.

The present invention is also directed to unique proteins, carbohydrates and lipids secreted by Lactobacilli. Although these secretions are capable of blocking bacterial adherence, they exhibit very little or no anti-microbial activity.

The present inventor has also surprisingly discovered that Lactobacilli are able to stimulate gut maturation.

The Lactobacillus strains, proteins, carbohydrates and lipids of the present invention may be used to treat adult and pediatric patients in intensive care units under total parenteral nutrition (intravenous feed) to avoid mucosal dysfunction and further bacterial translocation.

The Lactobacillus strains, proteins, carbohydrates and lipids of the present invention may also be used to treat patients undergoing chemotherapy, irradiation and bone marrow transplantation.

The Lactobacillus strains and secretions of the invention may be used to prevent and treat food allergy and intolerance, where injury caused by an antecedent bacterial infection allows the passage of food antigens through the gut mucosa and further triggers the inflammatory process.

The Lactobacillus strains and secretions of the invention may also be used to prevent and treat other GI disorders including but not limited to Celiac disease, where initial damage to the gut mucosa allows the passage of the triggering antigen to gain access to deeper layers of the intestine, which in turn, in concert with other immunologic, infective, or genetic factors can cause the clinical disease.

The Lactobacillus strains, proteins, carbohydrates and lipids of the present invention may also be used to prevent or treat other inflammatory diseases of the GI tract that may have a bacterial etiologic component.

The Lactobacillus strains, proteins, carbohydrates and lipids of the present invention may further be used in to treat fullterms, children, and adults, in GI dysfunctions of infective and/or inflammatory origin where bacterial infection may act as a trigger or aid in disease progression.

A preferred method of treating neonatal necrotizing enterocolitis comprises providing the Lactobacillus strains, proteins, carbohydrates and lipids of the invention for reducing inflammation caused by bacterial adherence, invasion and injury.

A preferred method of treating gastrointestinal dysfunctions includes providing the Lactobacillus strains, proteins, carbohydrates and lipids of the invention for improving physiological functions.

These and further and other objects and features of the invention are apparent in the disclosure, which includes the above and ongoing written specification, with the claims and the drawings.

DETAILED DESCRIPTION OF THE INVENTION

The present invention demonstrates that specific strains of Lactobacilli have the ability to reduce or block pro-inflammatory cytokines and induce anti-inflammatory cytokines. These effects have important ramifications in the host; and may be used as a vaccine against inflammatory diseases, as well as a therapeutic agent to reduce inflammation when the disease has already been established. The invention is also directed to unique proteins, carbohydrates and lipids secreted by these organisms. The proteins, carbohydrates and lipids, which are capable of blocking bacterial adherence and translocation/invasion, have very little or no antimicrobial activity.

The following Examples are provided for illustrative purposes only and are in no way intended to limit the scope of the present invention.

EXAMPLES

Two Lactobacillus strains L. plantarum and L. salivarius spp salivarius (assigned ATCC 202195 and ATCC 202196, respectively, by the American Type Culture Collection, 10801 University Blvd., Manassas, Va. 20110-2209 USA) were used in the following experiments:

Caco-2 cell Adherence Assay. A Caco-2 cell adherence assay was performed using standard techniques, E. coli was used as the adherent candidate Gram (−) organism according to Panigrahi et al., Occurrence of necrotizing entrocolitis may be dependent on patterns of bacterial adherence and intestinal colonization: Studies in Caco-2 tissue culture and weanling rabbit models, Pediatr. Res., 36:115–121 (1994). Briefly, mono- and co-infections of Caco-2 cells were performed with Lactobacillus strains L. plantarum and L. salivarius spp salivarius ($10^9$ organisms/ml) and E. coli ($10^8$ organisms/ml), followed by washing, fixing with ethyl alcohol and incubation with hyperimmune rabbit serum against E. coli. After further washings, monolayers were again incubated with FITC-anti-rabbit IgG (Fab specific). FIG. 1A shows the effect of concentrated media of Lactobacillus on adherence of 61 to Caco-2 cells. The results demonstrate that the number of E. coli adhering to Caco-2 cells was drastically reduced after co-infection with two Lactobacillus strains, i.e., L. plantarum and L. salivarius spp salivarius.

Caco-2 Cell Transwell System. A Caco-2 cell transwell system was used in accordance with Panigrahi et al., Development of an in vitro model for study of non-01 Vibrio cholerae virulence using Caco-2 cells, Infect. Immun., 58:3415–3424 (1990) and Panigrahi et al. (1994) to grow cells on a membrane allowing the measurement of bacteria that translocate. Briefly, Caco-2 cells were grown on polycarbonate filters in transwell clusters and TEER (transepithelial electrical resistance) was measured before and after Lactobacillus treatment.

Figure 1:
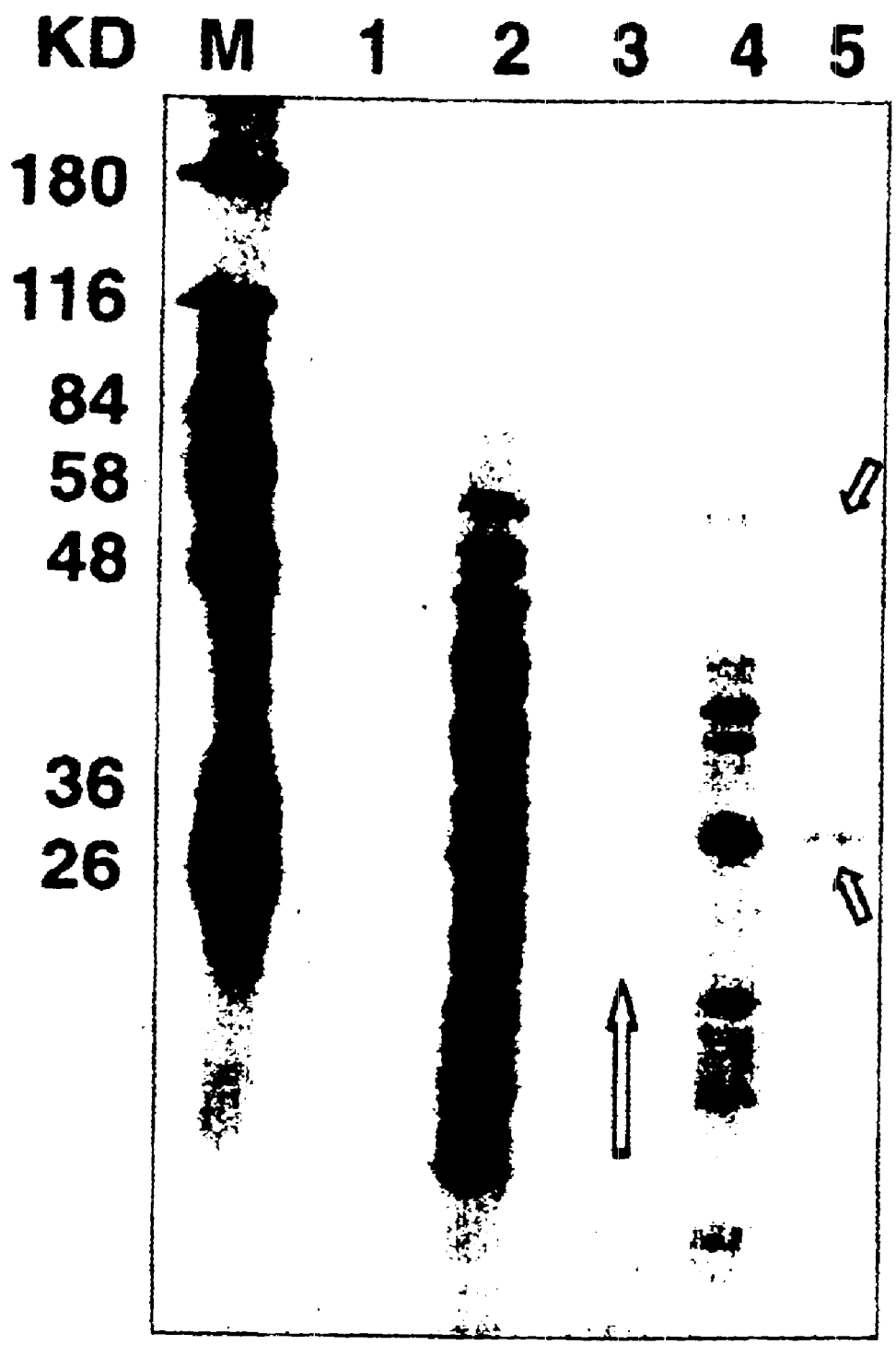
FIG. 1: Lactobacillus secreted factors from overnight growth in DMEM were seperated by PAGE (15%) and stained with Coomassie blue. M: molecular weight markers in kilo Dalton; Lane 1: DMEM (experimental medium) only; Lane 2: whole cell lysates of *L. plantarum*; Lane 3: secreted factors of *L. plantarum*; Lane 4: whole cell lysates of *L. salivarius* spp *salivarius*; Lane 5: secreted factors of *L. salivarius* spp *salivarius*. A protein with approximate molecular weight of 20 KD is identified in *L. plantarum* secretions (arrow). Two proteins with approximate molecular weights of 48 KD and 30 KD are identified in the secretions of *L. salivarius* spp *salivarius* (arrows).

Lactobacillus Secretions. Lactobacillus was grown in DMEM overnight from fresh plate cultures. The medium was centrifuged and clarified by passing through a 0.2 nm filter. Adherence assays were performed as previously described. FIG. 1 shows the proteins that have been secreted from both strains.

Figure 2:
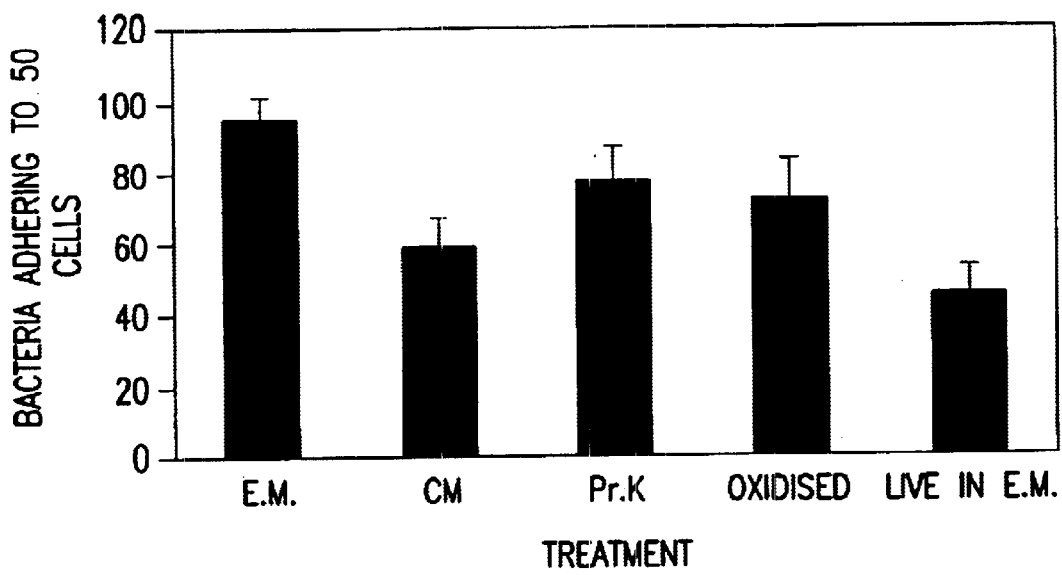
FIG. 2: Adherence assay using *E. coli* and *L. plantarum*-secreted factors. E.M.: experimental medium (DMEM only); CM: conditioned medium (from overnight culture of *L. plantarum*); Pr.K: conditioned medium treated with proteinase-K before the adherence assay. Oxidised: conditioned medium oxidized before the adherence assay; Live in EM: live bacteria (*L. plantarum*) with *E. coli*. Note the reduction in activity (blocking *E. coli*) after destroying the proteins and carbohydrates. These results suggest that the 20 KD protein and additional factor(s), carbohydrate in nature mediate the effects of *L. plantarum*.

FIG. 2 shows the effect of conditioned media of L. plantarum on adherence of E. coli to Caco-2 cells. The results show a significant reduction in E. coli adherence when Lactobacillus secretions were used. Note the reduction in activity (blocking E. coli) after destroying the proteins and carbohydrates. These results suggest that the 20 KD protein and additional factor(s), carbohydrate in nature mediate the effects of L. plantarum.

Figure 3:
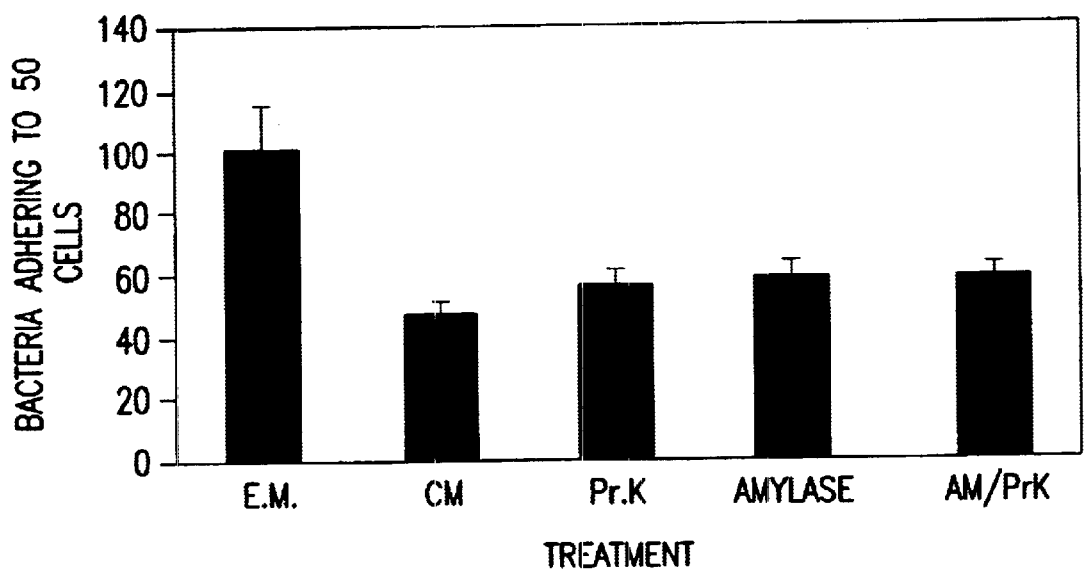
FIG. 3: Adherence assay using *E. coli* and *L. salivarius* spp *salivarius*—secreted factors. E.M.: experimental medium (DMEM only); CM: conditioned medium (from overnight culture of *L. salivarius*); Pr.K: conditioned medium treated with proteinase-K before the adherence assay. Amylase: conditioned medium treated with amylase to destroy the carbohydrates; Am/PrK: conditioned medium treated with amylase plus proteinase-K. Note a non-significant reduction in activity (blocking *E. coli*) after destroying the proteins and carbohydrates. Contrary to the results in FIG. 2, these data suggest that the *E. coli* blocking effects of *L. salivarius* are mediated by lipids.
Figure 4:
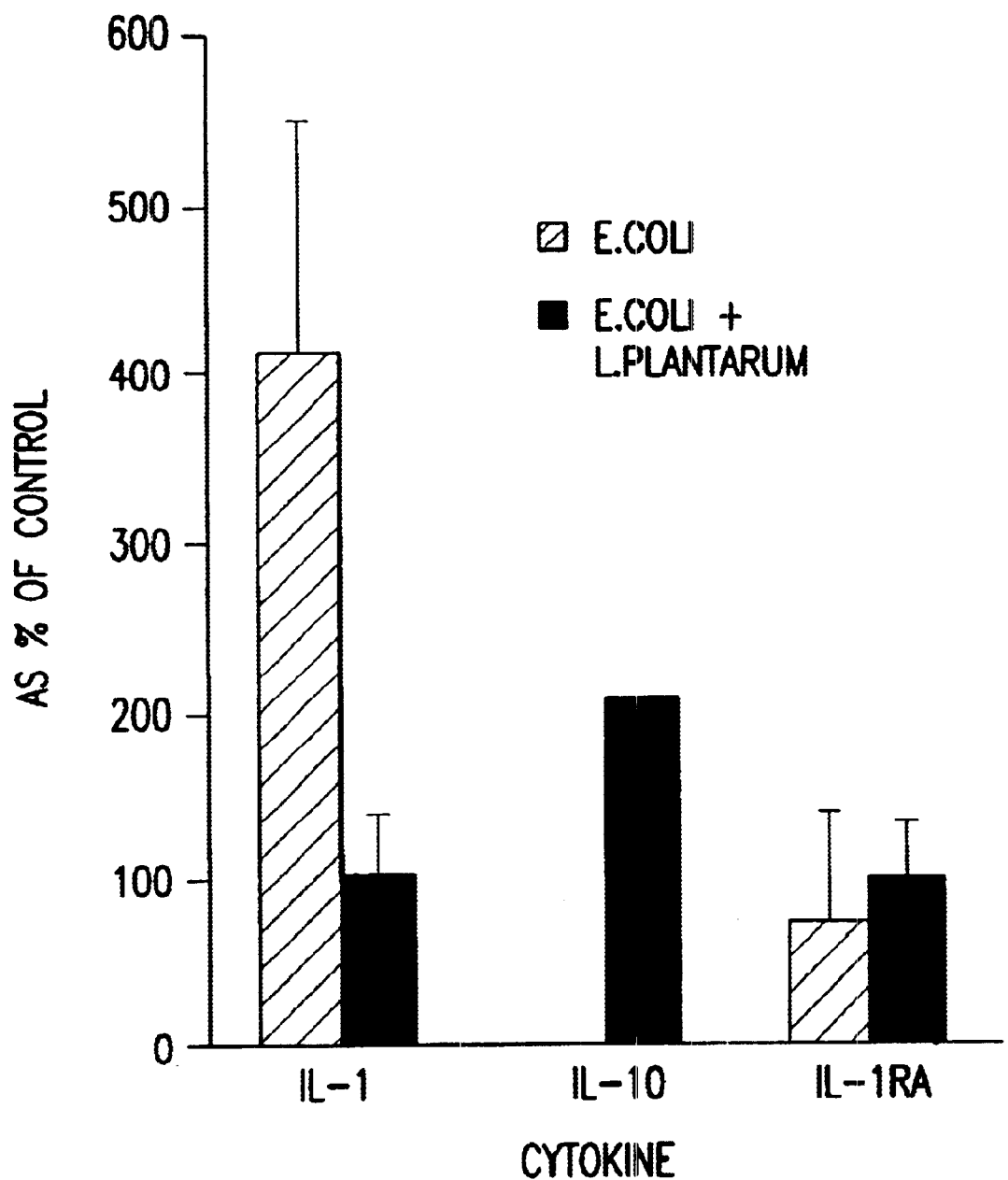
FIG. 4: Induction of cytokine mRNA in rabbit ileal loops infected with *E. coli* and a combination of *E. coli* and *L. plantarum*. There was a significant reduction of proinflammatory cytokine IL-1 after co-infection with *L. plantarum*. Anti-inflammatory cytokine IL-10 was induced only after co-infection with *L. plantarum*(*E. coli* alone did not induce IL-10). Also seen was an increased induction of IL-1RA (receptor antagonist) after co-infection with *L. plantarum*.
Figure 5:
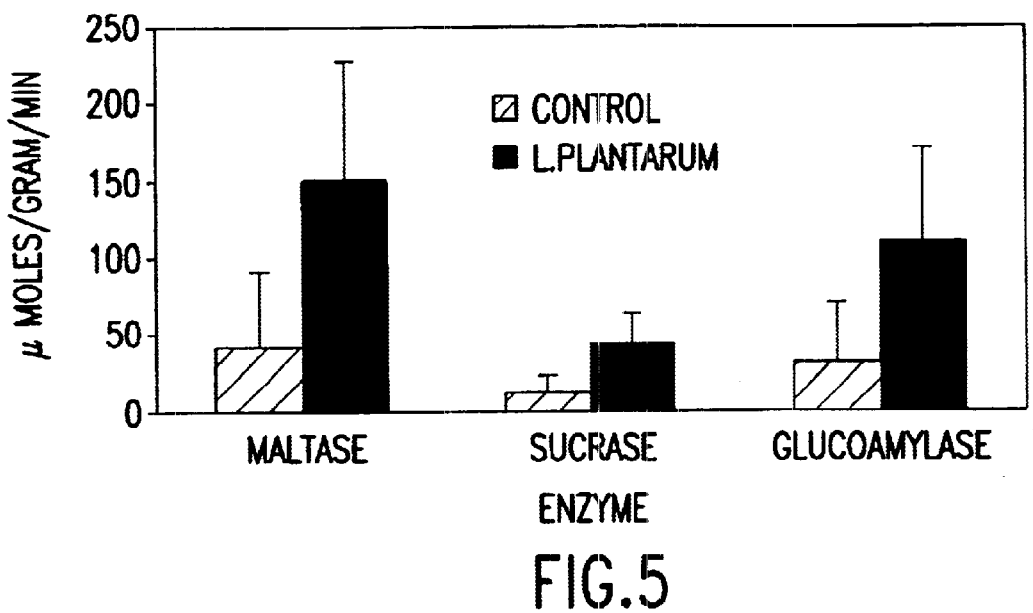
FIG. 5. Expression of small intestinal enzymes by Caco-2 cells. There was a significant increase in the expression of maltase, sucrase, and glucoamylase after the cells were treated with L. plantarum.
Figure 6:
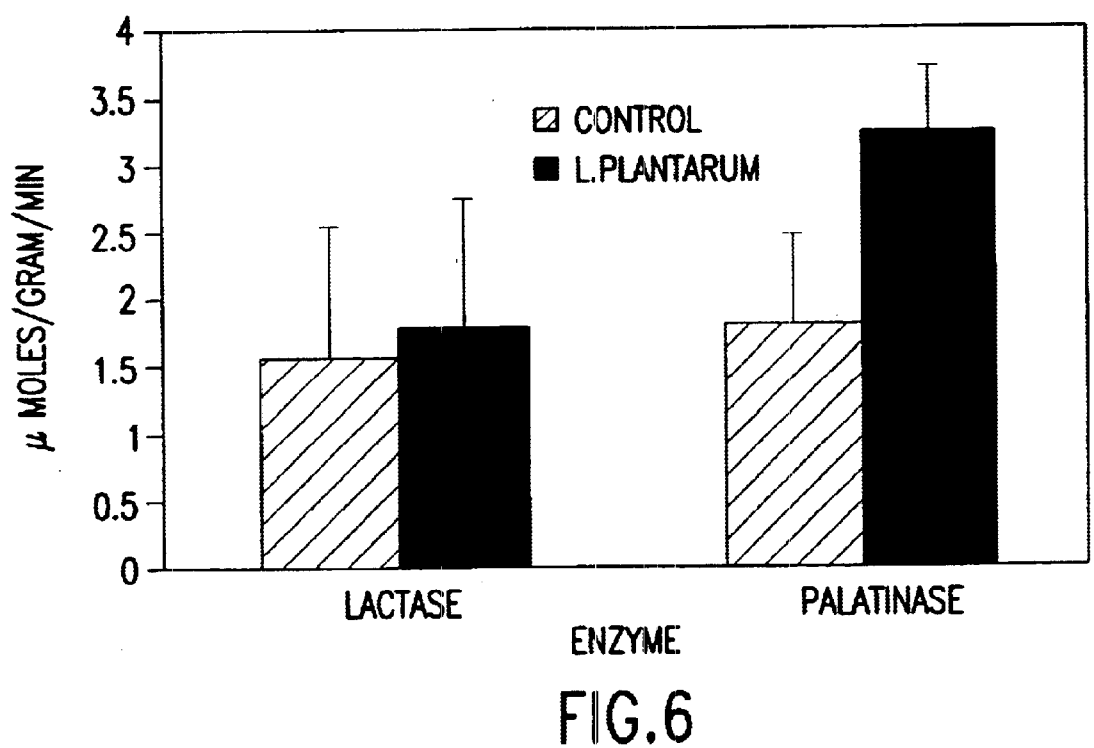
FIG. 6. Expression of small intestinal enzymes by Caco-2 cells. Note the increase in lactase and palatinase after treatment with L. plantarum.
Figure 7:
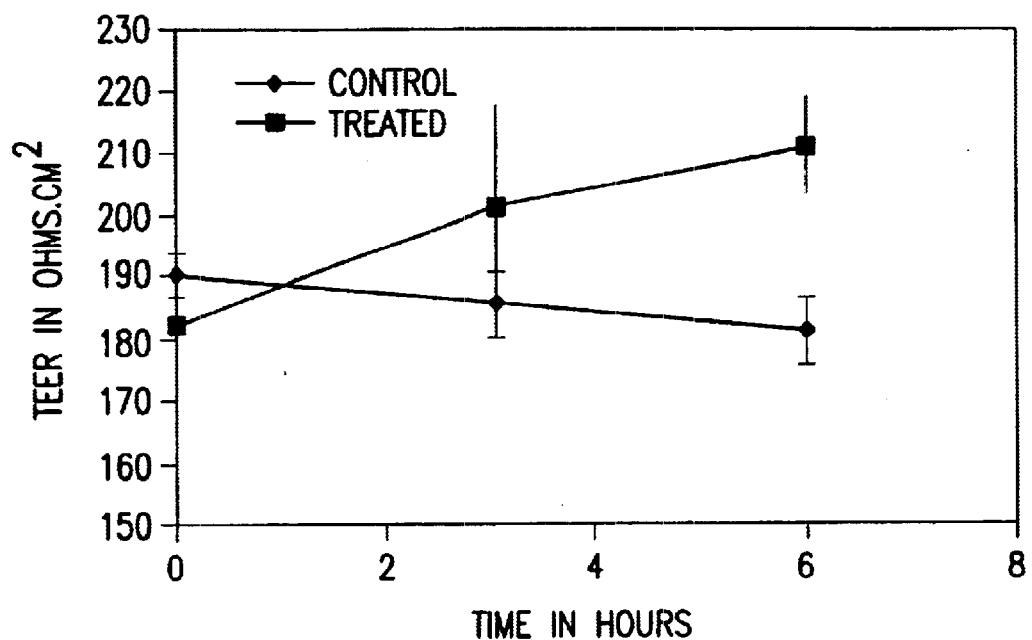
FIG. 7. TEER (trans epithelial electrical resistance) measurement after treatment with L. plantarum. There was a significant increase in TEER after 1 and 2 hours treatment with L. plantarum.
Figure 8:
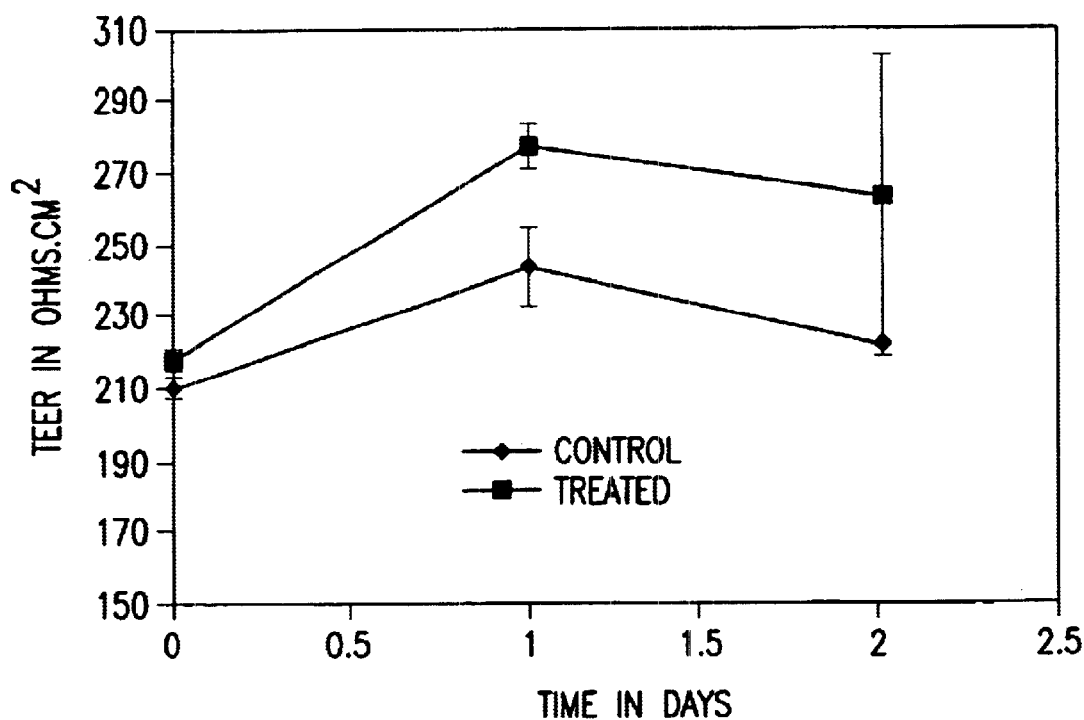
FIG. 8. Long term TEER (trans epithelial electrical resistance) measurement after treatment with L. plantarum. The increase in TEER was maintained over the 6 hr period after treatment with L. plantarum.

FIG. 3 shows the effect of conditioned media of L. salivarius spp salivarius on adherence of E. coli to Caco-2 cells. Note a non-significant reduction in activity (blocking E. coli) after destroying the proteins and carbohydrates. Contrary to the results in FIG. 2, these data suggest that the E. coli blocking effects of L. salivarius are mediated by lipids.

Anti-inflammatory Effects of Lactobacillus. The anti-inflammatory effects of Lactobacillus were determined in the rabbit ileal loop experiments by RT-PCR. The expression of pro-inflammatory cytokine IL-1 was significantly reduced after co-infection with L. plantarum. Anti-inflammatory cytokine IL-10 was induced only after co-infection with L. plantarum (E. coli alone did not induce IL-10). Also seen was an increased induction of IL-1RA (receptor antagonist) after co-infection with L. plantarum. The levels of these mRNAs were increased after E. coli infection.

There was an increase in the expression of IL-10 and IL-1RA (anti-inflammatory cytokines) and a decrease in the expression of pro-inflammatory cytokine IL-1 in these experiments. These results suggest that Lactobacilli may exert their beneficial effect by blocking bad cytokines and concurrently stimulating the expression of good cytokines.

Gut Maturation After Lactobacillus Treatment. Gut maturation after Lactobacillus treatment studies were performed in cultured Caco-2 cells grown in petri dishes or in transwell cultures. The trans-epithelial electrical resistance was significantly increased after treatment of the monolayers with L. plantarum. Expression of brush border specific enzymes (that are highly related to maturation) were assayed in control and Lactobacillus-treated cells. There was a significant increase in the expression of maltase, sucrase, glucoamylase and palatinase, and to a lesser extent lactase.

Weanling Rabbit Ileal Loop Experiment: Following previously described protocols, (Panigrahi P. Gupta S. Gewolb I H, and Morris J G Jr. 1994. Occurrence of Necrotizing Enterocolitis may be dependent on patterns of bacterial adherence and intestinal colonization: Studies in Caco-2 tissue culture and weanling rabbit models. Ped. Res. 36 (1):115–121), weanling rabbit ileal loops were infected with either E. coli alone or in combination with L. plantarum. After 12–16 hr, animals were euthanasized and segments of the loops were frozen in liquid nitrogen. RNA was extracted from pulverized intestinal segments, followed by cDNA synthesis and RT-PCR for cytokines.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

What is claimed is:

1. A method of reducing adherence or blocking translocation of bacteria, which are capable of causing necrotizing tissue injury in the mucosal cells of the gastrointestinal tract of a mammalian subject, said method comprising contacting mucosal cells of said mammalian host with cells and secretions of a Lactobacillus, said Lactobacillus being selected from the group consisting of *Lactobacillus plantarum*, deposited as ATCC 202195, and *Lactobacillus salivarius*, deposited as ATCC 202196.

2. The method of claim 1, wherein the blocking comprises blocking of the translocation of Gram negative bacteria.

3. A method of reducing adherence or blocking translocation of bacteria into mucosal cells of the gastrointestinal tract of a mammalian subject, said bacteria being capable of causing neonatal necrotizing enterocolitis, said method comprising contacting mucosal cells of said mammalian suject with cells and secretions of a Lactobacillus, said Lactobacillus being selected from the group consisting of *Lactobacillus plantarum*, deposited as ATCC 202195, and *Lactobacillus salivarius*, deposited as ATCC 202196.

4. A method of reducing adherence or blocking translocation of bacteria into the mucosal cells of the gastrointestinal tract of a mammalian subject, said bacteria being capable of causing gastrointestinal dysfunction in a said mammalian subject, said dysfunction characterized by infection or inflammation, said method comprising contacting mucosal cells of said mammalian suject with cells and secretions of a Lactobacillus, said Lactobacillus being selected from the group consisting of *Lactobacillus plantarum*, deposited as ATCC 202195, and *Lactobacillus salivarius*, deposited as ATCC 202196.

5. The method of claim 1, wherein said secretions are proteinaceous secretions.

6. The method of claim 3, wherein said secretions are proteinaceous secretions.

7. The method of claim 4, wherein said secretions are proteinaceous secretions.

* * * * *